(12) United States Patent
Pirli

(10) Patent No.: US 11,446,172 B2
(45) Date of Patent: Sep. 20, 2022

(54) WASTE DISPOSAL UNIT AS FUNCTIONAL UNDERPANTS

(71) Applicant: Aslan Ali Pirli, Gebze/Kocaeli (FR)

(72) Inventor: Aslan Ali Pirli, Gebze/Kocaeli (FR)

( * ) Notice: Subject to any disclaimer, the term of this patent is extended or adjusted under 35 U.S.C. 154(b) by 29 days.

(21) Appl. No.: 16/957,316

(22) PCT Filed: Nov. 29, 2018

(86) PCT No.: PCT/TR2018/000114
§ 371 (c)(1),
(2) Date: Jun. 23, 2020

(87) PCT Pub. No.: WO2020/022968
PCT Pub. Date: Jan. 30, 2020

(65) Prior Publication Data
US 2020/0345532 A1 Nov. 5, 2020

(30) Foreign Application Priority Data

Dec. 26, 2017 (TR) .................................. 2017/21930

(51) Int. Cl.
| | |
|---|---|
| *A61F 5/442* | (2006.01) |
| *A41B 9/12* | (2006.01) |
| *A61F 5/44* | (2006.01) |
| *A61F 5/453* | (2006.01) |
| *A61F 5/455* | (2006.01) |

(52) U.S. Cl.
CPC ................ *A61F 5/442* (2013.01); *A41B 9/12* (2013.01); *A61F 5/4408* (2013.01); *A61F 5/453* (2013.01); *A61F 5/455* (2013.01)

(58) Field of Classification Search
CPC ........ A61F 5/442; A61F 5/4408; A61F 5/453; A61F 5/455; A61F 5/451; A61F 5/44; A61F 5/03; A41B 9/12; A61G 9/00
See application file for complete search history.

(56) References Cited

U.S. PATENT DOCUMENTS

| | | | | |
|---|---|---|---|---|
| 3,522,808 | A * | 8/1970 | Worcester ............... | A61F 13/64 604/347 |
| 3,626,941 | A * | 12/1971 | Webb ....................... | A47K 7/08 604/347 |
| 4,776,848 | A * | 10/1988 | Solazzo ................... | A61F 5/453 604/213 |

(Continued)

FOREIGN PATENT DOCUMENTS

WO   WO-2007034774 A1 *  3/2007 ............. A61F 13/66

OTHER PUBLICATIONS

PCT International Search Report, Turkish Patent and Trademark Office (TURKPATENT), Application No. PCT/TR2018/000114, dated Feb. 5, 2020, 3 pages.

*Primary Examiner* — Benjamin J Klein
*Assistant Examiner* — Hans Kaliher
(74) *Attorney, Agent, or Firm* — Ziegler IP Law Group, LLC

(57) ABSTRACT

The present disclosure is for the patients who are not capable of going to the bathroom and not able to urinate physically, and being confined to bed; it relates to a waste disposal unit as functional underpants enabling the disposal of solid-liquid wastes of said patients in an autoregulatory manner, providing a full-hygienic cleaning for the person by means of adhering and contacting methods, and separately designed for males and females.

10 Claims, 11 Drawing Sheets

(56) References Cited

U.S. PATENT DOCUMENTS

| | | | | |
|---|---|---|---|---|
| 4,791,686 A | * | 12/1988 | Taniguchi | A61G 9/00 |
| | | | | 4/448 |
| 5,312,383 A | * | 5/1994 | Kubalak | A61F 5/4405 |
| | | | | 604/350 |
| 5,342,583 A | * | 8/1994 | Son | A61F 5/451 |
| | | | | 4/453 |
| 5,618,277 A | | 4/1997 | Goulter | |
| 6,554,817 B1 | * | 4/2003 | Oki | A61G 9/00 |
| | | | | 604/393 |
| 2002/0010446 A1 | * | 1/2002 | Maimets | A61F 5/451 |
| | | | | 604/355 |
| 2007/0142793 A1 | * | 6/2007 | Ben Youssef | A61F 5/455 |
| | | | | 604/329 |
| 2010/0010459 A1 | | 1/2010 | Piette et al. | |
| 2016/0346145 A1 | * | 12/2016 | Pirli | A61G 7/0509 |
| 2017/0312116 A1 | * | 11/2017 | Laniado | A61F 5/443 |

\* cited by examiner

WASTE DISPOSAL UNIT AS FUNCTIONAL UNDERPANTS

CROSS-REFERENCE TO RELATED APPLICATIONS

This application is a continuation-in-part application of, and claims the benefit of and priority to U.S. patent application Ser. No. 15/116,714, filed on Aug. 4, 2016, which is a National Stage Application of PCT/TR2015/000039 with a filing date of Feb. 4, 2015, now U.S. Pat. No. 10,478,358, which issued on Nov. 19, 2019. The instant application is a National Stage application of PCT/TR2018/000114 filed on Nov. 29, 2018, with a 371(c) date of Jun. 23, 2020

FIELD

The aspects of the disclosed embodiments are directed to a waste disposal unit for patients who are not capable of going to the bathroom, not able to urinate physically, and are confined to bed. The aspects of the disclosed embodiments relate to a waste disposal unit that is configured to serve as functional underpants for enabling the disposal of solid-liquid wastes of said patients in an autoregulatory manner, providing a full-hygienic cleaning for the person by means of adhering and contacting methods, and having different types of urine disposal apparatus separately designed for males and females. The aspects of the disclosed embodiments also eliminate the necessity of allocating an area for toilets in the space capsules in the space stations or during deep space trips and it will be adapted to the spacesuits due to its mobility feature.

BACKGROUND

Traditionally, the constant care for the patients who are not capable of going to the bathroom physically both in the hospital conditions and at homes brings about significant drawbacks and causes negative cases both for the patient and the ones who care for them. Considering the urinating problems, leakage of the urine onto the patient's clothes or to the outside areas or their problems to meet their excretion needs due to the physical inabilities, and the fact that women do not prefer to use public restrooms in their daily lives cause negative situations. Currently, also a tube or like are directed into the bladder during the use of the apparatus referred to as "catheter" which is used for even female patients whose urinary canal is not obstructed, which causes highly uncomfortable and painful cases, as well as infections. Male patients whose urinary canals are not obstructed use condom catheters. These types of catheters are fitted on the penis like a condom and thoroughly fixed to the penis by means of an adhesive in order to transversely adhere the end portion of the condom corresponding to the penis root. Therefore, the urine of the patient contacts with the periphery of the penis during sitting or lying down, which causes rashes and hygienic problems. The invention provides a significant easiness for the patients and patient relatives in terms of avoiding such problems.

SUMMARY

The product of the aspects of the disclosed embodiments has been designed with different features for males and females; it also may be produced with a contact-pressure effect which may be used to enable the hygienic disposal of the liquid wastes; and it has portions with an adhesive feature on the appropriate parts configured to be in contact with the periphery of the urinary outlet tract so as to prevent urine leakage. There are disposable apparatus with an adhesive feature, which have a urine reservoir with a closed end and with different types and sizes for males and females, which have stationary reservoirs and have been designed to be attached to the bladder, and which are able to be attached easily.

Several problems arising from the fact that the type used for males as a condom does not cover the penis thoroughly and tightly may be prevented.

By the aspects of the disclosed embodiments, it is possible to transfer the urine or sperm exiting the urine tract without any leakage by means of contacting through pressure or adhering around the hole where the urine exits. Also, it has the connection bays for the automatic or manual passage of the water by means of the sensor in order to clean the area where the urine comes out. The product of the present disclosure is made of a resilient material such as silicon and is not harmful for the patient.

DETAILED DESCRIPTION OF THE DISCLOSED EMBODIMENTS

Solid Waste Disposal Apparatus:

The aspects of the disclosed embodiments are directed to a solid waste pump or waste disposal unit configured as functional underpants which prevents limiting the human motions during disposing solid and liquid wastes. This is provided by an apparatus that enables fixing the waste disposal unit 10 on the human body.

Figure 1:
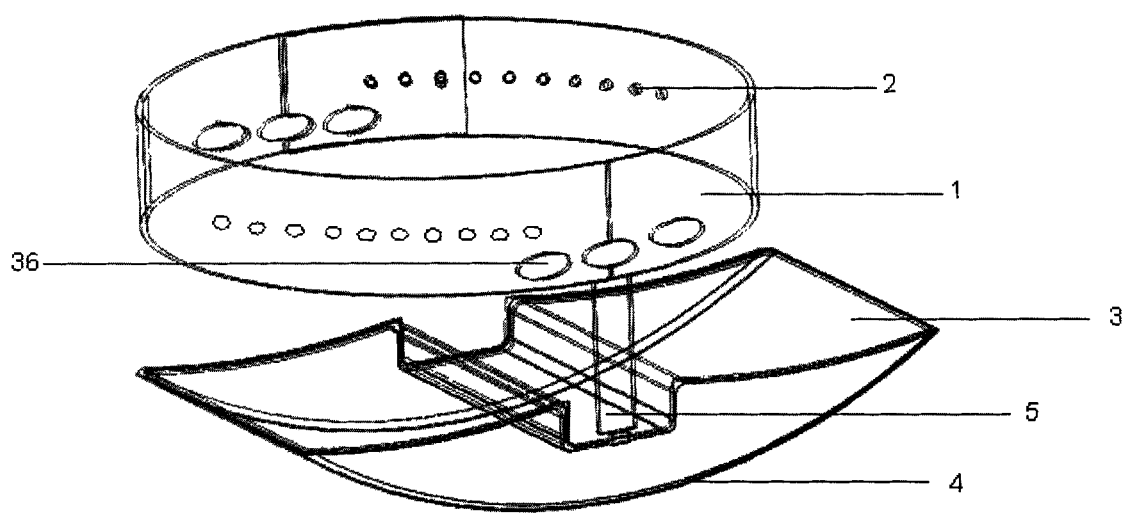
FIG. 1: General view of the apparatus on which the solid waste pump of the solid waste disposal unit is secured.
Figure 3:
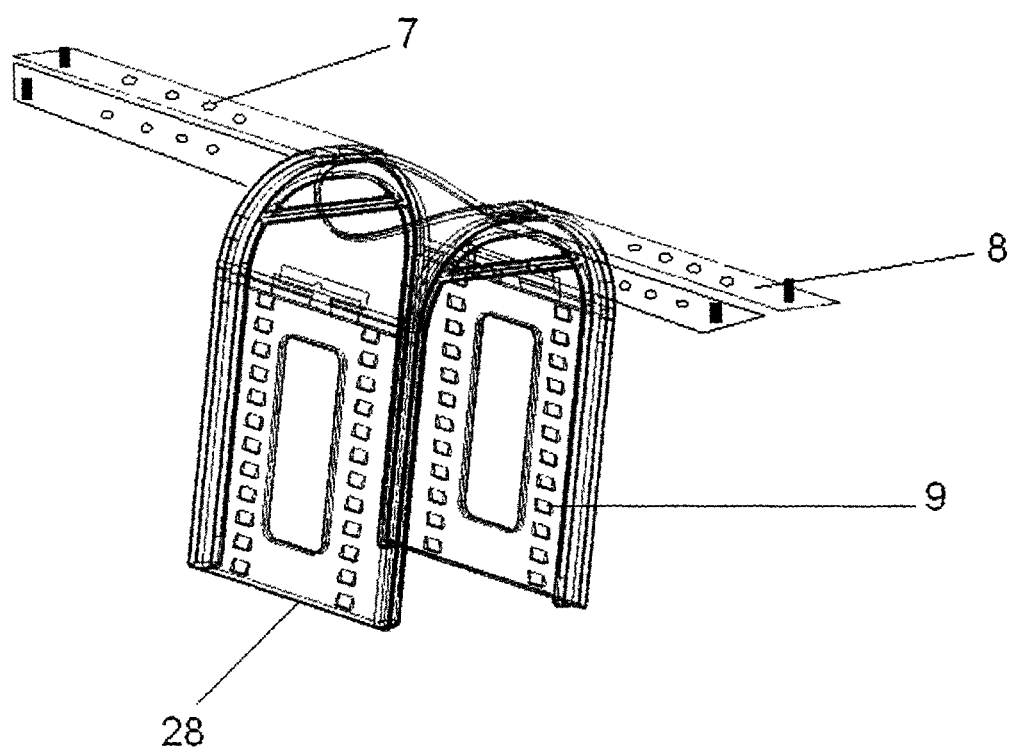
FIG. 3: General view of the pump housing.

As shown in FIG. 1, the waste disposal unit 10 is attached to a person by attaching the belt (1) having belt holes (2) thereon onto the waist of the human body. There are 3 elliptical strap fixation holes (36) both at the front and back portions on the belt (1). Referring to FIG. 3, the connection to the strap fixation hole (36) is provided by the adjustment through the straps (7-8) on the pump housing (28).

Figure 2:
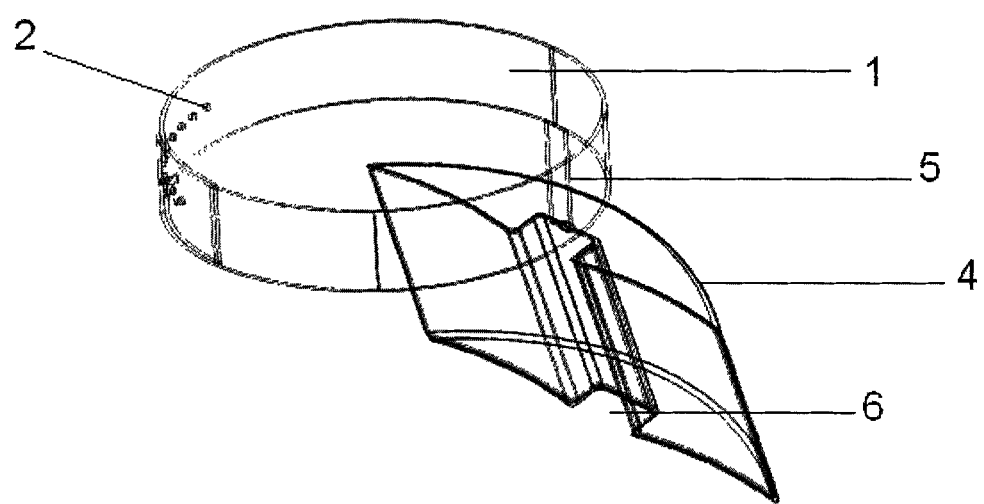
FIG. 2: The view of the apparatus on which the solid waste pump of the solid waste disposal unit is secured at standing position of the patient.

Referring also to FIG. 2, a hinged outer housing lid (4) and side flaps (3) are configured to be ergonomically fitting with the gluteal area, i.e. hip part of the human body. There is a conduit (6) to protect the solid waste pump equipment from the pressure that might be exerted in the sitting position.

Figure 4:
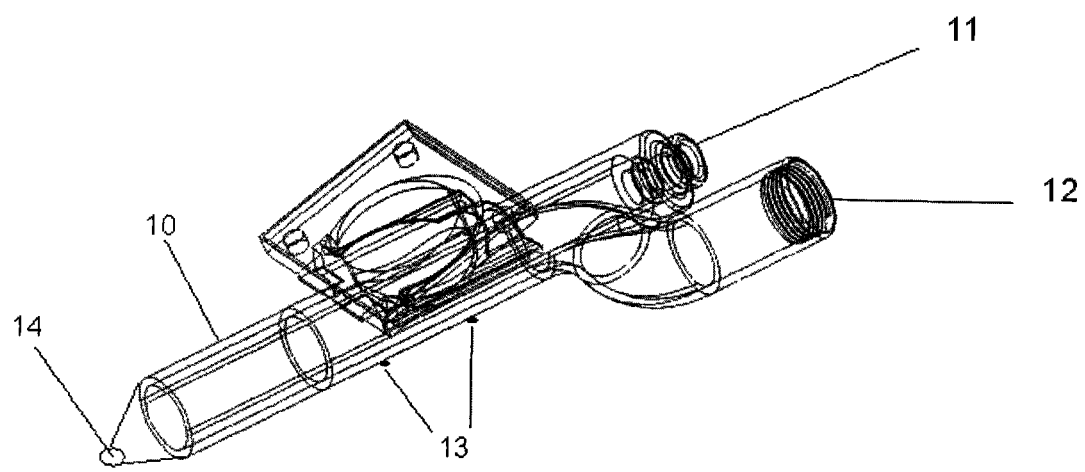
FIG. 4: General view of the solid waste pump.

The belt (1) is connected to the hinged outer housing lid (4) of the waste disposal unit by the connection part (5). The waste disposal unit (10) shown in FIG. 4 is protected from the pressure at walking, lying, or sitting positions, after the belt (1) is fixed on the waist of the human body. The hinged outer housing lid (4) may be positioned according to the standing or lying position of the human body (FIG. 1 and FIG. 2).

Referring to FIGS. 1 and 3, the pump housing (28) is secured into the elliptical holes (36) located on the belt (1), one of which is at front and the other at the back, by means of the straps (7, 8) having two resilient elastic flaps at both sides thereof. The distance between the waste disposal unit 10 and the anus is adjusted by means of the tabs (9) located on the pump housing (28). Thus, the waste disposal unit 10 is configured to be fixed to the anus and will not be affected by the physical motions of the human body (FIG. 3).

Figure 5:
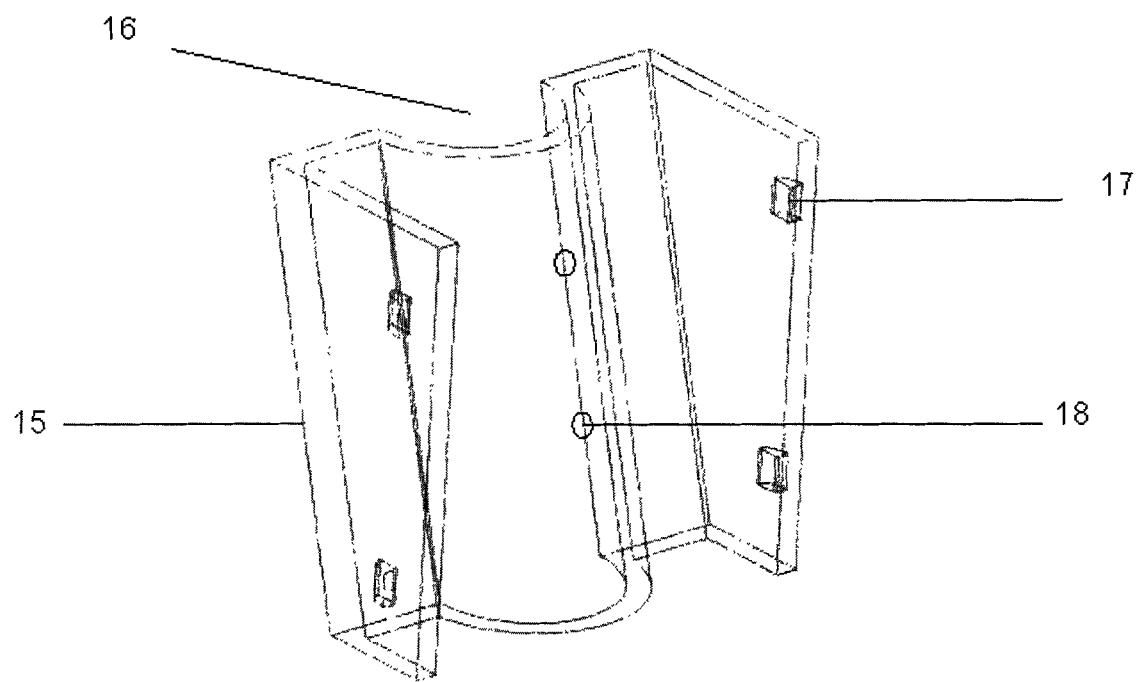
FIG. 5: General view of the pump fixation slide.

Referring to FIGS. 4 and 5, fixation pins (13) located on the waste disposal unit (10) engage with the fixation holes (18) on the distance adjusting apparatus (15). Thus, waste disposal unit (10) is fixed on the distance adjusting apparatus middle conduit (16) located in the middle of the distance adjusting apparatus (15). Then, distance adjusting apparatus (15) is attached to the tabs (9) on the pump housing (28) via side protrusions (17) located at the side portions thereof.

Figure 10:
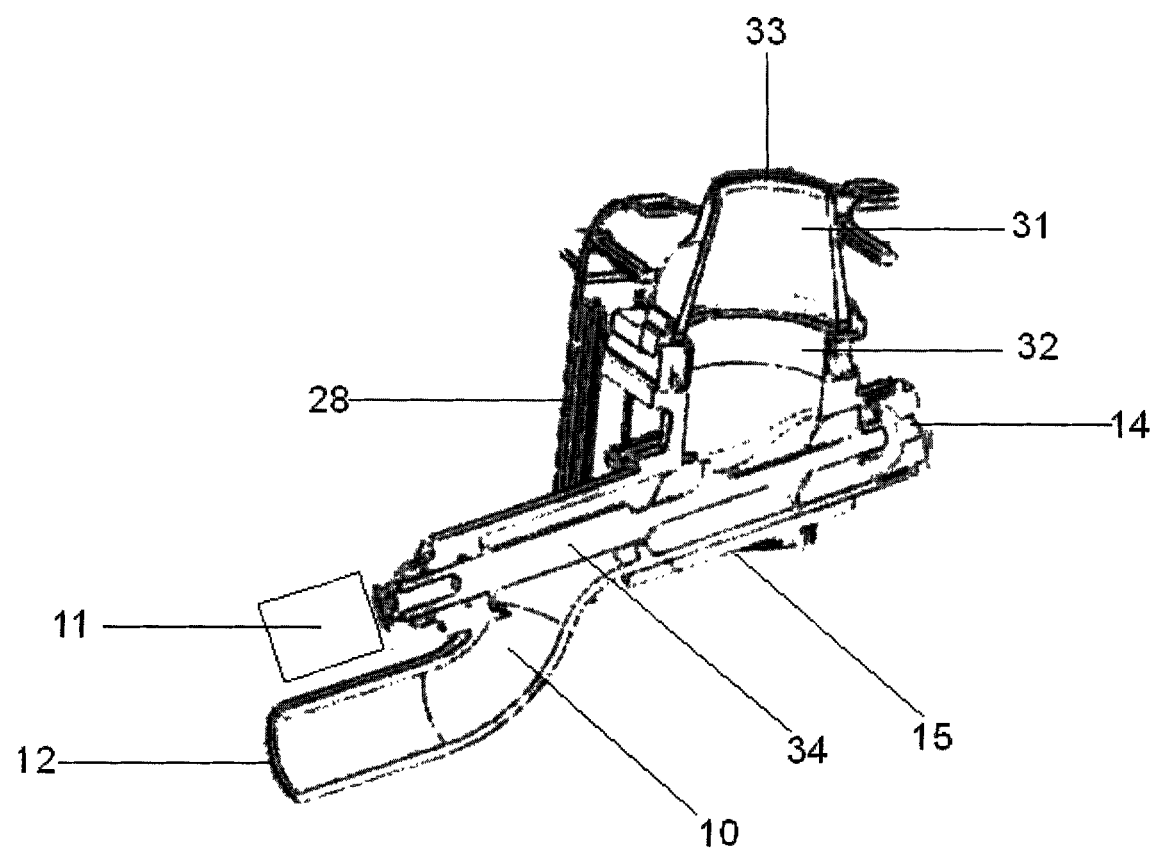
FIG. 10: Cross-sectional view of the solid waste pump

Referring to FIG. 10, by adjusting the distance, and transparent conical neck (31) with sensor secured on the waste disposal unit 10 and the silicon collar (33) secured on the top opening of the transparent conical neck (31) with sensor, the waste disposal unit 10 is configured to be secured on the anus without any contact with the anus.

The inner surface of the transparent conical neck (31) having a sensor and the anus are enabled to be washed together by means of the holes having different angles and located on the washing collar (32) below the transparent conical neck (31) having a sensor (FIG. 3, FIG. 4, FIG. 5, and FIG. 10).

Referring to FIGS. 4 and 10, in the waste disposal unit (10), there is a clean water inlet (14) providing the cleaning of the inside of the pump and an electromotor connection area (11) attached to the pump drill (34).

Urine Disposal Apparatus:

Operation of the portion of the invention which provides the urine disposal is different for males and females and said portion is designed differently for male and female patients.

Urine disposal apparatus for males: The urine disposal apparatus designed for males has the resilient disposable reservoir with an elastic feature which can be expanded during filling with urine or it has the tube end feature transferring the urine to the urine drainage bag. The end portion which is fixed on the penis is the same for both types.

Figures 6A, 6B:
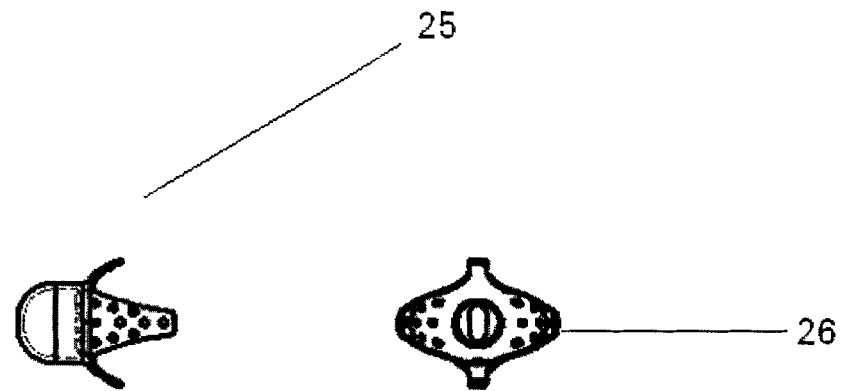
FIGS. 6*a*, 6*b*, 6*c*, and 6*d*: The view of the apparatus used as a condom for males.
Figure 6C:
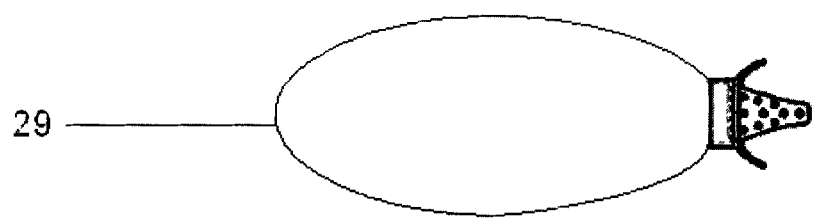
Figure 6D:
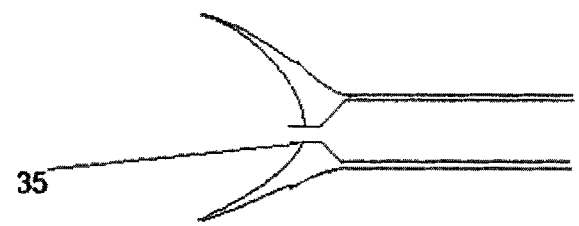

Referring to FIG. 6b, the urine disposal apparatus is secured onto the penis by means of the adhesive area (26) fitting well with the penis end. Also, as shown in FIG. 6d, hemispherical centering protrusion (35) of the urine hole (30) of the urine disposal apparatus, which may engage with the urine outlet at the end of the penis has the appropriate length (3-5 mm); and it is attached into the urine hole of the penis, thereby centering the condom onto the penis (FIG. 6d). Urine disposal apparatus designed for males has the ergonomic feature preventing urine leakage. The disposable type may have the reservoirs of different sizes.

The urine disposal apparatus (25) of FIG. 6a used as condom designed for males has a reservoir with a small volume. It is made of an elastic material and will have the adequate size to enable the urine or sperm to be filled into this reservoir. It will have the feature to be fixed only onto the head portion of the penis; its centering is enabled through the fixation and centering protrusion (35) by the adhesive area (26) fitting with the penis end, thereby preventing urine leakages or sperm leakage during sexual intercourse. The urine hole (30) located at the end of the urine disposal apparatus 25 should be placed such that the centering protrusion (35) corresponds to the urinary outlet hole at the end of the penis (FIGS. 6a, 6b, 6c, and 6d).

Figure 7A:
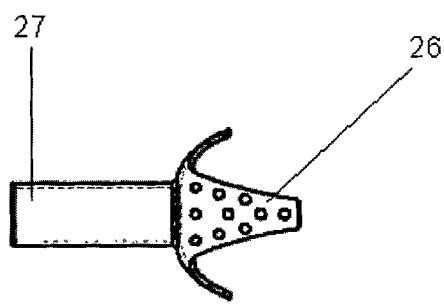
FIG. 7*a*, 7*b*, 7*c*: General view of the urine disposal apparatus for males
Figure 7B:
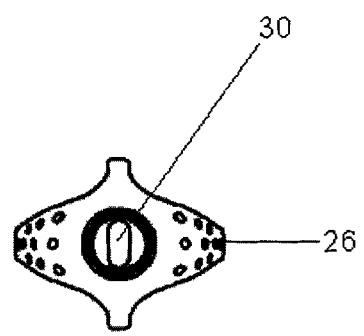
Figure 7C:
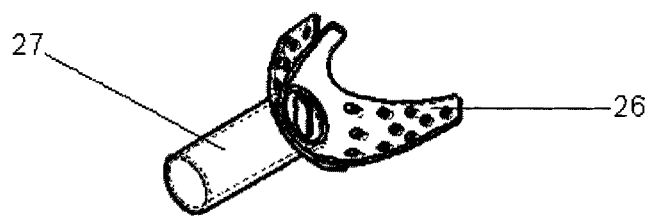
Figure 8A:
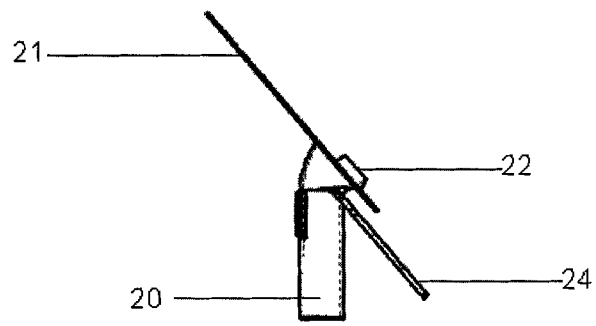
FIGS. 8*a*, 8*b*, 8*c*, and 8*d*: General view of the urine disposal apparatus for females
Figure 8B:
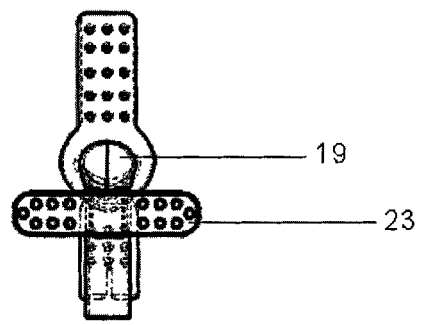
Figure 8C:
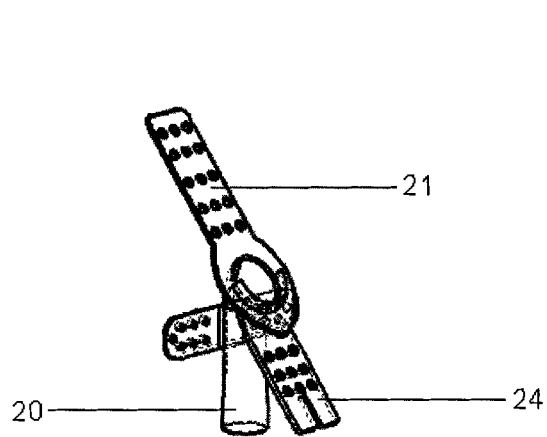
Figure 8D:
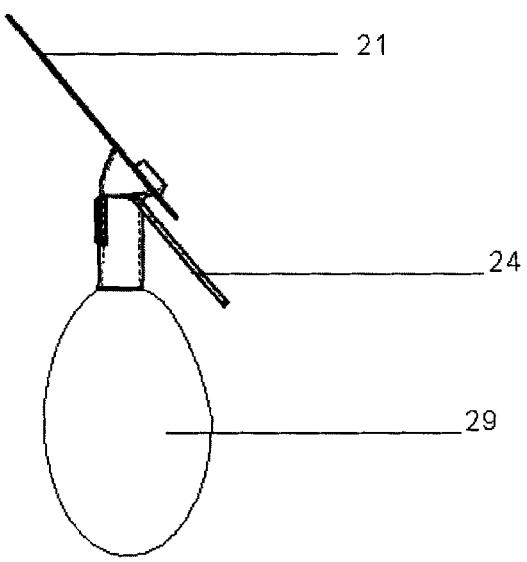
Figure 9:
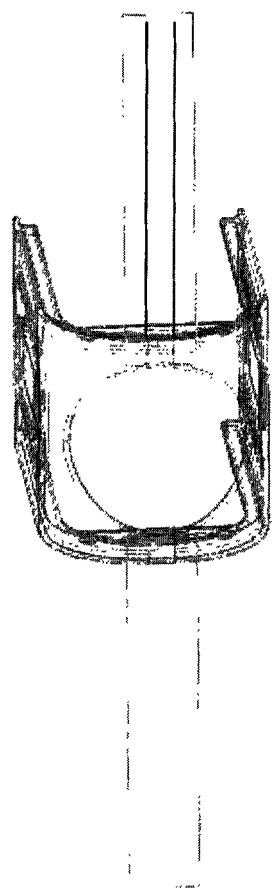
FIG. 9: Top view of the pump housing for wastes

Urine disposal apparatus for females: The urine disposal apparatus 25 designed for females fits with the protrusion (22) of FIG. 8a being in contact with the periphery of the urinary hole in the vagina. Thus, urine leakage would be avoided. There are adhesive flaps enabling the urine disposal apparatus 25 to be attached onto the human body, thereby preventing leakages. The urine disposal apparatus 25 is fixed to the patient by means of adhesive top flap (21) attached to the upper portion of the vagina, adhesive bottom flap (24) attached to the lower portion of the vagina, and adhesive side flaps (23) attached onto the outer surface of the labia on the both sides of the outer part of the vagina. Disposal of the urine is provided by urine outlet pipe (20). The urine disposal apparatus 25 for females is also designed as a disposable type like the one for the males (FIG. 7a, 7b, 7c).

Figure 11:
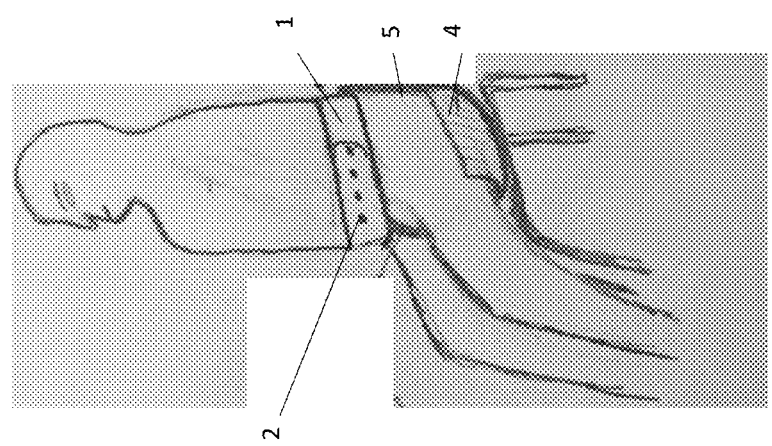
FIG. 11: General view of the apparatus in use

FIG. 11 illustrate the waste disposal unit 10 attached to a person. In this example, the belt 1 is shown attached around the waist of a person. The attachment member 5 runs between the belt 2 and the outer housing lid 4. The waste disposal unit 10 is not visible in this figure, but would be underneath the rear end of the person.

BRIEF DESCRIPTION OF THE PARTS INCLUDED

1—Belt
2—Belt holes
3—Side flaps
4—Hinged outer housing lid
5—Connection part
6—Conduit
7, 8—Straps
9—Tabs
10—Solid waste pump body
11—Electromotor connection area
12—Waste outlet
13—Fixation pins
14—Clean water inlet
15—Distance adjusting apparatus
16—Distance adjusting apparatus middle conduit
17—Side protrusions
18—Fixation holes
19—Urine outlet connection point
20—Urine outlet pipe
21—Adhesive top flap
22—Protrusion being in contact with the periphery of the urinary hole
23—Adhesive side flaps
24—Adhesive bottom flap
25—Condom apparatus
26—Adhesive area fitting with the penis end
27—Waste reservoir connection part
28—Pump housing
29—Urine reservoir
30—Urine hole
31—Transparent conical neck with sensor
32—Washing collar
33—Silicon collar
34—Pump drill
35—Centering protrusion
36—Strap fixation hole

The invention claimed is:

1. A waste disposal unit configured as functional underpants, the waste disposal apparatus comprising;
   a belt comprising belt holes and strap fixation holes;
   a hinged outer housing lid, side flaps, a conduit located at a middle of the side flaps of which a solid waste pump body is located, a connection part connecting the belt and the hinged outer housing lid, a pump housing coupled to the conduit, the solid waste pump body connected to the pump housing, and a distance adjusting apparatus connected to the pump housing;
   b) a urine disposal apparatus for females comprising:
      a protrusion configured to fit with a urinary hole of a vagina by contacting the urinary hole, an adhesive top flap configured to attached to a upper portion of the vagina, an adhesive bottom flap configured to be attached to a lower portion of the vagina, and adhesive side flaps configured to be attached onto an outer surface of the labia on both sides of an outer part of the vagina; and
      a urine outlet pipe that is attached to the protrusion, and
   c) a urine disposal apparatus for males comprising an adhesive area configured to fit with a penis end, urine hole, centering protrusion, and urine outlet pipe.

2. The waste disposal unit according to claim 1, wherein the urine disposal apparatus for males comprises urine reservoir with a resilient elastic feature.

3. The waste disposal unit according to claim 1 wherein a distance between the solid waste pump body and the anus is configured to be adjusted by the tabs on the pump housing.

4. The waste disposal unit according to claim 1 wherein the hinged outer housing lid is configured to be positioned in accordance with an upright or lateral position of a person.

5. The waste disposal unit according to claim 1 wherein the pump housing is secured to the pump body by attaching tabs on both ends of resilient elastic straps to the strap fixation holes located at a front and a back on the belt.

6. The waste disposal unit according to claim 1 wherein fixation pins located on the solid waste pump body are attached to fixation holes on the distance adjusting apparatus and the solid waste pump body is secured to the distance adjusting apparatus and the conduit.

7. The waste disposal unit according to claim 1 wherein the distance adjusting apparatus is attached to tabs on the pump housing via side protrusions located on side portions of the pump housing.

8. The waste disposal unit according to claim 1 wherein the solid waste pump body comprises a clean water inlet and an electromotor connection configured to be connected to a pump drill.

9. The waste disposal unit according to claim 1 wherein the solid waste pump body further comprises a transparent conical neck with a sensor and a silicon collar located above the transparent conical neck are configured to be secured without any contact with the anus by means of the distance adjusting apparatus.

10. The waste disposal unit according to claim 9 wherein an inner portion of the transparent conical neck can be washed by means of holes with different angles located on a washing collar below the transparent conical neck.

* * * * *